US006348607B1

(12) United States Patent
Müller et al.

(10) Patent No.: US 6,348,607 B1
(45) Date of Patent: Feb. 19, 2002

(54) METHOD FOR OXIDIZING AN ORGANIC COMPOUND HAVING AT LEAST ONE C-C DOUBLE BOND

(75) Inventors: Ulrich Müller, Neustadt; Georg Heinrich Grosch, Bad Dürkheim; Bernd Stein, Seeheim-Jugenheim; Norbert Rieber, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/806,514

(22) PCT Filed: Oct. 14, 1999

(86) PCT No.: PCT/EP99/07738

§ 371 Date: Apr. 16, 2001

§ 102(e) Date: Apr. 16, 2001

(87) PCT Pub. No.: WO00/21945

PCT Pub. Date: Apr. 20, 2000

(30) Foreign Application Priority Data

Oct. 15, 1998 (DE) .......................................... 198 47 629

(51) Int. Cl.⁷ ..................... C07D 301/08; C07D 301/10
(52) U.S. Cl. ........................ 549/523; 549/532; 549/533; 549/536
(58) Field of Search ................................ 549/523, 532, 549/533, 536

(56) References Cited

U.S. PATENT DOCUMENTS

| 5,599,955 A | * | 2/1997 | Nora et al. ................... 549/529 |
| 5,625,084 A | * | 4/1997 | Pitchai et al. ................ 549/536 |

FOREIGN PATENT DOCUMENTS

| EP | 484136 | * | 6/1992 |
| EP | 709360 | * | 1/1996 |
| EP | 916403 | * | 5/1996 |
| EP | 850986 | * | 6/1998 |
| GB | 960332 | * | 6/1964 |
| GB | 970878 | * | 9/1964 |
| WO | WO 98/00413 | | 1/1998 |
| WO | WO 98/00415 | | 1/1998 |

* cited by examiner

*Primary Examiner*—Ba K. Trinh
(74) *Attorney, Agent, or Firm*—Oblon, Spivak, McClelland, Maier & Neustadt, P.C.

(57) ABSTRACT

In a process for oxidizing an organic compound containing at least one C—C double bond, or a mixture of two or more thereof, which comprises the step (II) below:

(II) reaction of the organic compound or the mixture of two or more thereof with a medium comprising molecular oxygen in the presence of a heterogeneous catalyst, the medium further comprises carbon monoxide (CO).

8 Claims, No Drawings

METHOD FOR OXIDIZING AN ORGANIC COMPOUND HAVING AT LEAST ONE C-C DOUBLE BOND

This is a 371 of PCT/EP99/07738 dated Oct. 14, 1999.

The present invention relates to a process for oxidizing an organic compound containing at least one C—C double bond, or a mixture of two or more thereof, in which the organic compound or the mixture of two or more thereof is reacted with a medium comprising molecular oxygen and carbon monoxide in the presence of a heterogeneous catalyst. In addition, the present invention also relates to an integrated process of the abovementioned type in which the used catalyst is regenerated and any components which have not been consumed are separated off and returned to the reaction.

Processes for oxidizing an organic compound containing at least one C—C double bond, in particular olefins and among these preferably propylene, are known. Thus, U.S. Pat. No. 5,625,084 describes the reaction of propylene to form propylene oxide. There, propene is reacted with oxygen over silver-containing catalysts to give propylene oxide. However, selectivities of propene to propylene oxide of only from 50 to 60% at low conversions are achieved in this reaction. A large amount of the expensive propene cannot be converted into the target product propylene oxide.

EP-A 0 709 360 and WO 98/00413 describe the preparation of propylene oxide from propylene using an explosive gas mixture of oxygen and hydrogen over Au/Ti catalysts. However, such processes demand elaborate and costly safety measures.

An integrated process for preparing epoxides from alkanes is described in EP-A 0 850 936. The epoxidation is carried out by bringing a gas comprising the alkene, hydrogen and unreacted alkane into contact with oxygen in the presence of an Au-containing cataylst.

It is an object of the present invention to provide a simple process of the above-described type which, without suffering from the disadvantages of the use of explosive oxygen/hydrogen mixtures, is able to convert olefins into the corresponding epoxides with selectivities significantly above 60%.

We have found that this object is achieved by a process for oxidizing an organic compound containing at least one C—C double bond, or a mixture of two or more thereof, which comprises the step (II) below:

(II) reaction of the organic compound or the mixture of two or more thereof with a medium comprising molecular oxygen in the presence of a heterogeneous catalyst, wherein the medium further comprises carbon monoxide (CO).

The molecular oxygen used according to the present invention for the oxidation is subject to no restrictions of any sort. Accordingly, it is possible to use air, essentially pure molecular oxygen or oxygen which originates from other sources, e.g. ozone and nitrogen oxides, although preference is given to molecular oxygen.

Furthermore, it is essential according to the present invention for the medium to comprise carbon monoxide (CO). This too can originate from any source. The CO used preferably comes from a synthesis gas process.

Further processes from which the CO can originate are described, for example, in K. Weissermel, H. J. Arpe, Industrial Organic Chemistry, $2^{nd}$ edition (1993), VCH Verlag Weinheim, p.14 ff., the full scope of which is hereby incorporated by reference into the present application.

In addition, the medium may comprise hydrogen or water, preferably in the form of water vapor, or else hydrogen and water. The source of hydrogen and water is likewise subject to no restrictions of any sort, although the hydrogen is particularly preferably prepared in situ by, for example, dehydrogenation of alkanes which are then used as starting materials.

Furthermore, the medium used according to the present invention may further comprise a gaseous or liquid diluent such as helium, nitrogen, argon, methane, carbon dioxide, water vapor or a mixture thereof, preferably water vapor and/or carbon dioxide (in the gas phase). When carrying out the reaction in the liquid phase or supercritically, it can be carried out in the presence of an oxidation-stable and thermally stable liquid, e.g. chlorinated aliphatic alcohols such as chloropropanol, chlorinated aromatics such as chlorobenzene or dichlorobenzene and also liquid polyethers, polyesters and polyalcohols.

The ratio of the essential components in the process of the present invention, i.e. the ratio of organic compound to oxygen to CO, can be selected freely. It is preferably 1:0.1–10:0.1–10, more preferably 1:1.5–5:0.3–3 and in particular 1:2:0.5 (in each case organic compound:$O_2$:CO).

There are also, in principle, no restrictions of any sort in respect of the organic compounds containing at least one C—C double bond which can be used for the purposes of the present invention. The term "organic compound containing a C—C double bond" used in the context of the present invention encompasses all organic compounds which contain at least one C—C double bond. The compound can be a low molecular weight organic compound, i.e. a compound which has a molecular weight of up to about 500, or a polymer, i.e. a compound which has a molecular weight of more than 500. However, the process of the present invention is preferably employed for low molecular weight organic compounds of the above-described type. Suitable organic compounds include linear, branched or cyclic compounds which can have aromatic, aliphatic, cycloaliphatic groups or a combination of two or more thereof. The organic compound used preferably has from 2 to 30 carbon atoms, more preferably from 2 to 10 carbon atoms. It is preferably an aliphatic monoolefin. However, it is also possible for the organic compound used to have more than one ethylenically unsaturated double bond, as is the case for, for example, dienes or trienes. It can contain additional functional groups, e.g. a halogen atom, a carboxyl group, an ester group, a hydroxyl group, an ether bridge, a sulfide bridge, a carbonyl group, a cyano group, a nitro group, an amino group or a combination of two or more thereof. The double bond can be terminal or internal. Furthermore, it can be a constituent of a cyclic structure as is the case for, for example, cyclohexene. It is also possible to use a mixture of two or more compounds of this type.

Further examples of suitable organic compounds include unsaturated fatty acids or their derivatives, e.g. esters and glycerides of such unsaturated fatty acids, and also oligomers or polymers of unsaturated organic compounds, e.g. polybutadiene.

Examples of such organic compounds include the following: ethylene, propylene, 1-butene, cis- and trans-2-butene, isobutylene, butadiene, pentenes, isoprene, 1-hexene, 3-hexene, 1-heptene, 1-octene, diisobutylene, 1-nonene. 1-decene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, dimers, trimers or tetramers of propylene, styrene and other vinylaromatic organic compounds having at least one C—C double bond, diphenylethylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylene-cyclopentane, methylenecyclohexane, vinylcyclohexane, vinylcyclohexene, methallyl ketone, allyl chloride, allyl bromide, acrylic acid, methacrylic acid, crotonic acid, vinylacetic acid, crotyl chloride, methallyl chloride, dichlorobutenes, allyl alcohol, allyl carbonate, allyl acetate, alkyl acrylates and methacrylates, diallyl maleate, diallyl phthalate, unsaturated triglycerides such as soya oil, unsaturated fatty acids such as oleic acid, linoleic acid, linolenic acid, ricinoleic acid and also their esters including the monoglyceryl, diglyceryl and triglyceryl esters.

It is also possible to use mixtures of two or more compounds of this type, in particular mixtures of the compounds mentioned above by way of example.

Accordingly, the present invention particularly preferably provides a process of the type spoken of here in which the organic compound containing at least one C—C double bond is selected from the group consisting of linear or branched aliphatic olefins, linear or branched aromatic olefins, linear or branched cycloaliphatic olefins, each having up to 30 carbon atoms, and mixtures of two or more thereof.

The process of the present invention is particularly useful for the reaction of low molecular weight olefins such as ethylene, propylene and the butenes, particularly preferably propylene.

The catalysts used in the step (II) of the process of the invention are microporous and/or mesoporous and/or macroporous solids which preferably comprise at least one element of group VIIIa or Ib or at least one element of each of groups VIIIa and Ib, preferably solids comprising silver and/or gold, particularly preferably gold. The above catalysts preferably contain Au and/or Ag in amounts of in each case from about 0.01 to about 20% by weight, preferably from about 0.1 to about 5% by weight and in particular from about 0.3 to about 1% by weight.

In addition, the catalysts used can further comprise the elements Si, Al, Ti, Zr or mixtures thereof.

In a further embodiment of the process of the invention, the catalysts used further comprise elements of groups Ia, IIa, IIIa, rare earth elements from the lanthanide and actinide series or mixtures thereof.

Furthermore, they can further comprise elements of groups IVa, Va, VIa, VIIa, IIb, IIIb, IVb, Vb, VIb and VIIb.

Specific examples of particularly preferred catalysts are:
transition metal-containing zeolites as are described in DE-A 197 23 950;
gold-containing catalysts comprising a support based on titanium dioxide, as described in EP-A 0 709 360;
gold-containing titanium silicalites, preferably microporous or mesoporous titanium silicalites of the structure TS-1, TS-2, Ti-β, Ti-ZSM-48 or Ti-MCM-41, as described in WO 98/00413;
likewise gold-containing catalysts on a titanium-containing support material which further comprises a "promoter" metal selected from main groups I and II of the Periodic Table of the Elements or from among the rare earth metals of the lanthanide and actinide series; supports which are suitable for this catalyst include titanium dioxide, titanium silicalites, titanates of the "promoter" metals, titanium dispersed on $SiO_2$, and silicates of the "promoter" metals; such catalysts are described in WO 98/00414;
catalysts as are described in WO 98/00415 which comprise gold on a support comprising titanium dispersed on silicon dioxide;
catalysts based on silver applied to an alkaline earth metal carbonate which comprise both a potassium salt and a molybdenum promoter, as are described in U.S. Pat. No. 5,625,084.

The full contents of the abovementioned publications relating to catalysts and their preparation are incorporated by reference into the present application.

According to the present invention, particular preference is given to using catalysts which comprise a silicon dioxide having mesopores or both mesopores and micropores. The mesopore-containing catalysts based on silicon dioxide are subject matter of EP-A-0 831 059, whose full contents relating to the catalysts and their preparation are incorporated by reference into the present application.

The catalysts based on a silicon dioxide having micropores and mesopores are subject matter of the application DE-A 198 47 630.2 filed in parallel to the present application, whose full contents are incorporated by reference into the present application. In this parallel application, the contents of EP-A 0 831 059 relating to the starting compounds and preparative methods are incorporated by reference, but in the preparation of silicon dioxide containing mesopores and micropores the preparation, i.e. the reaction of the starting materials, is carried out at a pH of <7. The silicon dioxide obtained in this way has, in one embodiment, at least one of the following properties (i) to (iii):

(i) a sum of the specific surface areas of the micropores and mesopores of at least 300 $m^2/g$;
(ii) a sum of the pore volumes of the micropores and mesopores of at least 0.2 ml/g;
(iii) a maximum in the pore diameter distribution of the mesopores at at least 3 nm.

The upper limit for the pore volumes of the micropores and mesopores is 1.5 ml/g. The upper limit for the sum of the specific surface areas of the abovementioned pores is 1000 $m^2/g$. The maximum in the pore diameter distribution of the mesopores can be up to 50 nm.

The process described there also makes it possible to prepare silicon dioxides containing mesopores and micropores whose surface area is at least 200 $g/cm^2$ or even at least 100 $g/cm^2$, with the upper limit preferably being below 500 $g/cm^2$.

For the purposes of the present invention "mesopores" are pores having a diameter in the range from 2 to 50 nm and "micropores" are pores having pore diameters of less than 2 nm. The pore diameters and specific surface areas of the mesopores are measured by nitrogen adsorption at 77 K. The surface area of the pores can be calculated using the BJH model (DIN 66134). The pore volume is determined at a relative pressure of $p/p_0=0.98$.

If the reaction of step (II) is carried out as a fixed-bed process, preference is given to using a particularly mechanically stable catalyst. Suitable catalysts are, in particular, catalysts having a zeolite structure as are described in DE-A 196 23 611.8, the full contents of which relating to catalysts are likewise incorporated by reference into the present application. The catalysts described therein have been shaped by strengthening shaping processes; in this respect, it is in principle possible to use all methods which are generally customary in the case of catalysts for achieving shaping together with strengthening, e.g. extrusion.

When carrying out the reaction as a fixed-bed reaction, it is possible to use any shaped bodies having sufficient stability and comprising the abovementioned active components. The shaped catalyst bodies can either be produced directly from the noble metal-containing catalyst powder or the abovementioned noble metals are applied after the shaping step to the shaped body which comprises the abovementioned activity-promoting elements. The noble metal-containing catalyst powders or the noble metal-free powders comprising the abovementioned activity-promoting elements can be either applied to shaped bodies, introduced into them or shaped to form such shaped bodies.

The shaping of the noble metal-containing catalyst powder or the noble metal-free powder comprising the abovementioned activity-promoting elements can be carried out by extrusion, tableting or the like. Before extrusion, the powders to be shaped are processed to produce formable compositions with the aid of, preferably, a make-up liquid and, if desired, using one or more additives by means of a compaction step, e.g. using a kneader or a pan mill. For tableting, it is likewise possible, if desired, to add one or more additives which have, inter alia, lubricating properties to the powder to be shaped.

To increase the strength of the shaped body, inorganic or organic materials can be added during shaping to the powder to be shaped. These materials can likewise increase the abrasion resistance when the powder is applied to existing shaped bodies by means of a suitable process step such as spraying, high coating or the like.

Furthermore, the powder to be shaped or to be applied can also be introduced into shaped bodies. For this purpose, organic or inorganic materials can be polymerized in the presence of the powder in such a way that the resulting polymer encloses the powder firmly but leaves it accessible to the reactants.

If the shaping, application or introduction of the powder is carried out using noble metal-free powder comprising the abovementioned activity-promoting elements, the noble metal components are applied after shaping, application or introduction of the powder. Methods of applying the noble metal component can be impregnation, steeping, ion exchange, vapor deposition or the like. If desired, the noble metal components applied in this way can then, if they are not in active form, be converted into an active form by subsequent treatment of the noble metal-containing shaped body, e.g. by calcination, reduction, oxidation or the like. Subsequent treatment may also be necessary in the case of shaped bodies which have been produced by shaping noble metal-containing powders. Furthermore, the catalysts produced by strengthening shaping processes as described in DE-A 196 23 609.6 or DE 197 23 751.7 can also be used. Here too, the above-cited applications are fully incorporated by reference into the present application.

The reaction of step (II) over the catalyst used according to the present invention can be carried out in the gaseous, supercritical or liquid phase.

The process is generally carried out at from 0 to 300° C., preferably from about 40 to about 180° C., more preferably from about 50 to about 150° C. and particularly preferably from about 60 to about 100° C. In the case of a reaction in the liquid phase, temperatures below 100° C. are generally employed. The pressures used in the reaction according to the present invention are from about 0.01 to about 1 MPa.

The process of the invention can be carried out continuously or batchwise. Furthermore, bringing the catalyst into contact with the organic compound and bringing this compound into contact with the medium comprising carbon monoxide and oxygen can be carried out at different times or physically separately.

In the process of the present invention, particularly after a long operating time when the selectivity and/or activity of the catalyst used in the reaction has decreased, the catalyst can also be regenerated. Here, it is possible to regenerate the catalyst by treatment with a gas stream suitable for the regeneration, in particular an oxygen-containing gas stream, more preferably an oxygen-containing gas stream where the oxygen has been produced by decomposition of nitrogen oxides, at from 100° C. to 600° C. This catalyst can then be reused. The regeneration can also be carried out in the actual reactor. The composition of the gas stream used for the regeneration is chosen so as to eliminate the causes of deactivation. In the case of deactivation caused by carbon deposits, the catalyst is exposed to a gas stream comprising oxygen or substances which supply oxygen. If the deactivation has occurred as a result of oxidation of the noble metal component, the gas stream can comprise reducing substances, e.g. hydrogen. It may also be necessary to redisperse the noble metal component during the regeneration. In this case, use is made of compounds which are suitable for dispersing the abovementioned noble metal components. In addition, a washing procedure with solvents, e.g. water, alcohols, aldehydes, ketones, etc., can also be carried out in the context of the regeneration. Further details regarding such a regeneration may be found in DE-A 197 23 950 and DE-A 197 23 949. Furthermore, the regeneration processes described in EP-A 0 790 075 and EP-A 0 743 094 can also be used.

Accordingly, the present invention also provides an integrated process for oxidizing an organic compound containing at least one C—C double bond, or a mixture of two or more thereof, which comprises the steps (I) to (IV) below:

(I) preparation of a medium comprising molecular oxygen and carbon monoxide;

(II) reaction of the organic compound or the mixture of two or more thereof with the medium comprising molecular oxygen and carbon monoxide in the presence of a heterogeneous catalyst;

(III) regeneration of the at least partially deactivated catalyst which has been used in step (II); and (IV) carrying out the reaction of step (II) using a catalyst comprising the catalyst regenerated in step (III).

In addition, the integrated process of the present invention can also comprise the step (V) below:

(V) separation of unconsumed molecular oxygen or carbon monoxide or unreacted organic compound or unconsumed molecular oxygen and carbon monoxide and unconsumed starting material from the medium and return of the molecular oxygen which has been separated off, the carbon monoxide which has been separated off or the unreacted organic compound or a mixture of molecular oxygen, carbon monoxide and unreacted organic compound to step (II).

If, in the process of the present invention, the organic compound containing at least one C—C double bond is selected from the group consisting of linear or branched aliphatic olefins, linear or branched aromatic olefins and linear or branched cycloaliphatic olefins, each having up to 30 carbon atoms, i.e. if an olefin is used for the reaction with the hydroperoxide, this can be obtained by dehydrogenation of the corresponding saturated organic compound so as to give the olefin and hydrogen.

Such processes for converting an alkane into the corresponding olefin are known per se, especially with regard to propane dehydrogenation. They are known in the literature under the names STAR, CATOFIN® or OLEFLEX® processes and are described in detail in, for example, Chem. Systems Report 91-5, 1992, p.50 ff. In addition, they are referred to in numerous patents, e.g. U.S. Pat. No. 4,665,267 or EP-A 0 328 507 and also U.S. Pat. No. 4,886,928.

A characteristic of these processes is that the alkane is dissociated in an endothermic reaction to give the olefin, i.e., for example, propane to propene, and hydrogen. Widely used catalysts for these processes are zinc and aluminum spinels with noble metal doping, chromium oxide/aluminum oxide and supported platinum catalysts.

Furthermore, promoted iron oxide catalysts for carrying out alkane dehydrogenations are known from DE-A 39 23 026.

The olefin preferably used as starting material, in particular propylene, can also be obtained from the corresponding saturated hydrocarbon by steam cracking or catalytic cracking. These cracking processes can also be operated so as to give not only propene, but also CO in addition to propene. Such processes are described in K. Weissermel, H. J. Arpe, Industrial Organic Chemistry, $2^{nd}$ edition (1993), VCH Verlag Weinheim, p.17 ff., the full scope of which is hereby incorporated by reference into the present application. Further details regarding such processes may be found, for example, in U.S. Pat. No. 5,599,955 and U.S. Pat. No. 5,599,956 and the prior art cited therein; the full contents of these publications, including the prior art cited therein, relating to this aspect of the present invention are incorporated by reference into the present application.

Particularly when carrying out the process of the invention as an integrated process, i.e. as a process in which the volume flows are all closed, it is advantageous for the olefin to be used in the epoxidation step, in particular propylene, to be obtained by dehydrogenation of the corresponding saturated organic compound, since the epoxidation step also tolerates the unreacted alkane from the dehydrogenation step still present in the olefin and thus saves an expensive alkane/olefin, in particular propane/propene, separation.

The hydrogen originating from the alkane dehydrogenation can also be used directly in hydrogen peroxide production, e.g. in the anthraquinone process or a process starting from the elements. Of course, it is also possible to use the CO from the cracking processes.

Furthermore, the endothermic step of alkane dehydrogenation can be coupled with the exothermic reaction of step (II) in an integrated heat and energy system.

As already indicated above, the process of the invention is particularly suited to being carried out as an integrated process, i.e. as a multistage process in which the streams of the various components used during the process are partly or completely closed. It is also preferred for the above integrated process to be operated using appropriate heat and energy coupling in which the energy liberated in the exothermic process steps (II) and (III) is used directly for operating the endothermic step (I).

The present invention is illustrated by the examples below.

EXAMPLES

Example 1

Preparation of the Catalyst 504 g of tetraethoxysilane, 70.4 g of tetraisopropyl orthotitanate, 720 g of ethanol and 146 g of isopropanol were mixed in a 4 l glass flask fitted with a stirrer. A solution of 120 g of dodecylamine and 17.6 g of hydrochloric acid (10% strength by weight) in 1560 g of deionized water was added to this mixture. After stirring for 20 hours at room temperature, the white precipitate was filtered off, washed with water until neutral and dried in air. To remove the organic components, the dried product was then calcined in air for 5 hours at 500° C. The titanium content was 6.7% by weight.

Gold was applied to the resulting solid by dissolving 0.426 g of tetrachloroauric acid (Chempur) in 1600 g of water, adjusting the pH to 7.2 using 0.1 mol/l sodium hydroxide solution and adding the freshly calcined titanium-containing powder. This suspension was stirred for 1 hour at 70° C., then cooled, decanted and filtered and the filtercake was washed a number of times with water.

The resulting solid was dried at room temperature under reduced pressure and calcined in air for 12 hours at 400° C.

The pinkish violet powder contained 0.87% by weight of gold, 25 ppm of chlorine, 6.2% by weight of titanium.

Example 2

Oxidation Using CO and $O_2$ in the Presence of Water Vapor

A gas-phase tube reactor (internal diameter: 6 mm, length: 200 mm) was charged with the catalyst from Example 1 (2 g of 0.1 mm size fraction) and, at 60° C., a mixture of 10 standard ml/min of propene, 20 standard ml/min of $O_2$, 5 standard ml/min of CO and 10 standard ml/min of Ar was passed through it. Before entering the reactor, the gas stream was saturated with water at room temperature. After a reaction time of 3 hours, the following were found in a gas sample of the product: 200 ppm of PO, 10 ppm of acrolein, 6 ppm of acetone and <5 ppm of propionaldehyde.

Example 3

Use of CO from Synthesis Gas

A gas-phase tube reactor (internal diameter: 6 mm, length: 200 mm) was charged with the catalyst from Example 1 (2 g of 0.1 mm size fraction) and, at 60° C., a mixture of 10 standard ml/min of propene, 20 standard ml/min of $O_2$, 5 standard ml/min of CO and 10 standard ml/min of Ar was passed through it. After a reaction time of 3 hours, the following were found in a gas sample of the product: 153 ppm of PO, 5 ppm of acrolein, 7 ppm of acetone and <5 ppm of propionaldehyde.

Comparative Example

The same catalyst and the same conditions as in Example 3 were used, but only oxygen and no synthesis gas was metered in.

After a running time of 3 hours, a sample was taken from the reaction gas and analyzed. No propylene oxide, acrolein or acetone above the detection limit (5 ppm) were found. Only at elevated temperatures of from 90 to 150° C. were the oxidation products acrolein and acetone obtained in higher concentrations. Propylene oxide was not formed.

What is claimed is:

1. A process for oxidizing an organic compound containing at least one C—C double bond, or a mixture of two or more thereof, which comprises the step (II) below:

(II) reaction of the organic compound or the mixture of two or more thereof with a medium comprising molecular oxygen in the presence of a heterogeneous catalyst, wherein the medium further comprises carbon monoxide (CO)

characterized in that the carbon monoxide used originates from a synthesis gas process, and wherein the heterogeneous catalyst comprises a silicon dioxide having mesopores or both mesopores and micropores.

2. A process as claimed in claim 1, where the medium comprises not only carbon monoxide and oxygen but also hydrogen or water or hydrogen and water.

3. A process as claimed in claim 1, wherein the heterogeneous catalyst comprises at least one element of group VIIIa or Ib of the Periodic Table of the Elements or at least one element from each of groups VIIIa and Ib of the Periodic Table of the Elements.

4. A process as claimed in claim 1, wherein the reaction of step (II) is carried out in the gaseous, supercritical or liquid phase.

5. A process as claimed in claim 1, wherein the reaction of step (II) is carried out continuously or batchwise.

6. A process as claimed in claim 1, wherein the contacting of the heterogeneous catalyst with the organic compound or the mixture of two or more thereof and the contacting of the organic compound or the mixture of two or more thereof with the medium comprising molecular oxygen and carbon monoxide which are carried out during the reaction are carried out at different times or physically separately.

7. An integrated process for oxidizing an organic compound containing at least one C—C double bond, or a mixture of two or more thereof, which comprises the steps (I) to (IV) below:

(I) preparation of a medium comprising molecular oxygen and carbon monoxide;

(II) reaction of the organic compound or the mixture of two or more thereof with the medium comprising molecular oxygen and carbon monoxide in the presence of a heterogeneous catalyst;

(III) regeneration of the at least partially deactivated catalyst which has been used in step (II); and (IV) carrying out the reaction of step (II) using a catalyst comprising the catalyst regenerated in step (III).

8. A process as claimed in claim 7 which further comprises the step (V) below:

(V) separation of unconsumed molecular oxygen or carbon monoxide or unreacted organic compound or unconsumed molecular oxygen and carbon monoxide and unconsumed starting material from the medium and return of the molecular oxygen which has been separated off, the carbon monoxide which has been separated off or the unreacted organic compound or a mixture of molecular oxygen, carbon monoxide and unreacted organic compound to step (II).

* * * * *